United States Patent
Prendergast et al.

(10) Patent No.: US 6,216,966 B1
(45) Date of Patent: Apr. 17, 2001

(54) DISPENSING DEVICES

(75) Inventors: Maurice Joseph Prendergast, Bracknell; Michael Leslie Green, Nannerch, both of (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/297,476

(22) Filed: Oct. 8, 1999

(30) Foreign Application Priority Data

Oct. 30, 1996 (GB) .................................................. 9622623

(51) Int. Cl.⁷ ...................................................... B05B 5/00
(52) U.S. Cl. .......................... 239/690; 239/708; 222/137; 222/631; 222/260
(58) Field of Search ..................... 239/690, 708, 239/99; 222/137, 631, 401, 635, 260

(56) References Cited

U.S. PATENT DOCUMENTS

| | | |
|---|---|---|
| 2,570,774 | 10/1951 | Davis . |
| 3,900,138 | 8/1975 | Phillips . |
| 3,997,113 * | 12/1976 | Pennebaker, Jr. ................... 239/708 |
| 4,549,243 | 10/1985 | Owen et al. . |
| 4,561,037 | 12/1985 | Owen . |
| 4,621,268 | 11/1986 | Keeling et al. . |
| 4,663,639 | 5/1987 | Owen . |
| 5,222,664 * | 6/1993 | Noakes et al. ....................... 239/690 |
| 5,292,067 | 3/1994 | Jeffries et al. . |
| 5,341,990 * | 8/1994 | Konieczynski ....................... 239/708 |
| 5,405,090 * | 4/1995 | Greene et al. ....................... 239/690 |
| 5,490,633 | 2/1996 | Jeffries et al. . |
| 5,630,793 * | 5/1997 | Rowe ..................................... 604/20 |
| 5,813,614 * | 9/1998 | Coffee ................................... 239/690 |
| 5,857,456 * | 1/1999 | Sun et al. ........................ 128/203.15 |

FOREIGN PATENT DOCUMENTS

| | | |
|---|---|---|
| 0 224 352 | 6/1987 | (EP) . |
| 0 441 501 | 8/1991 | (EP) . |
| 0 468 735 | 1/1992 | (EP) . |
| 0 468 736 | 1/1992 | (EP) . |
| 0 510 725 | 10/1992 | (EP) . |
| 0 544 549 | 6/1993 | (EP) . |
| 0 678 337 | 10/1995 | (EP) . |
| 2 700 279 | 7/1994 | (FR) . |
| 53 845 | 3/1968 | (LU) . |
| WO 96 40441 | 12/1996 | (WO) . |

OTHER PUBLICATIONS

SU 1 061 847 A (Taru Univ) Dec. 23, 1983.

* cited by examiner

*Primary Examiner*—Patrick Brinson
*Assistant Examiner*—Dinh Q. Nguyen
(74) *Attorney, Agent, or Firm*—Leonard W. Lewis; Paul M. Ulrich

(57) ABSTRACT

An electrostatic spraying device comprising a nozzle, means for establishing a column of material to be sprayed within a passage leading to the nozzle outlet such that the leading surface of the column is spaced from the nozzle outlet, means for pneumatically ejecting said column or part thereof from the nozzle and means for applying high voltage to the material so that the spray formed by breaking up of the column on ejection from the nozzle are electrically charged. The column of material in the passage is preferably a discreet slug having a leading surface spaced from the nozzle outlet and a trailing surface to which air, gas or vapor under pressure can be applied to effect ejection of the slug from the nozzle.

24 Claims, 3 Drawing Sheets

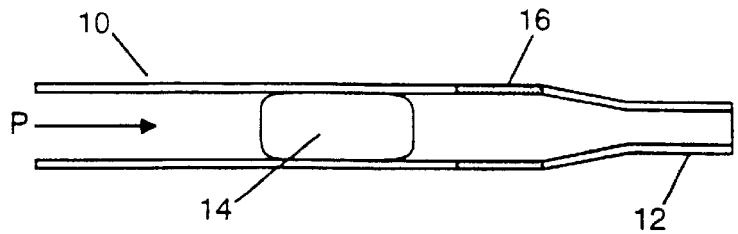
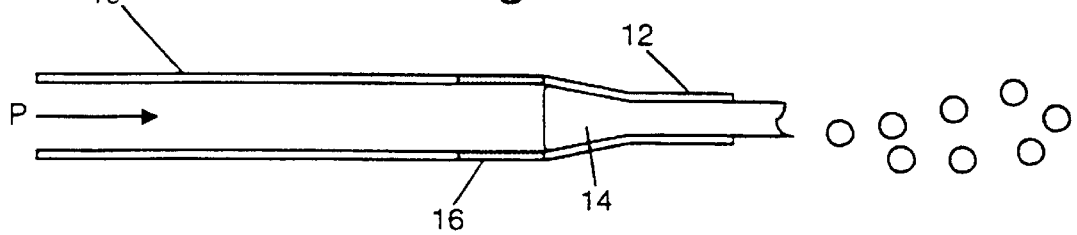
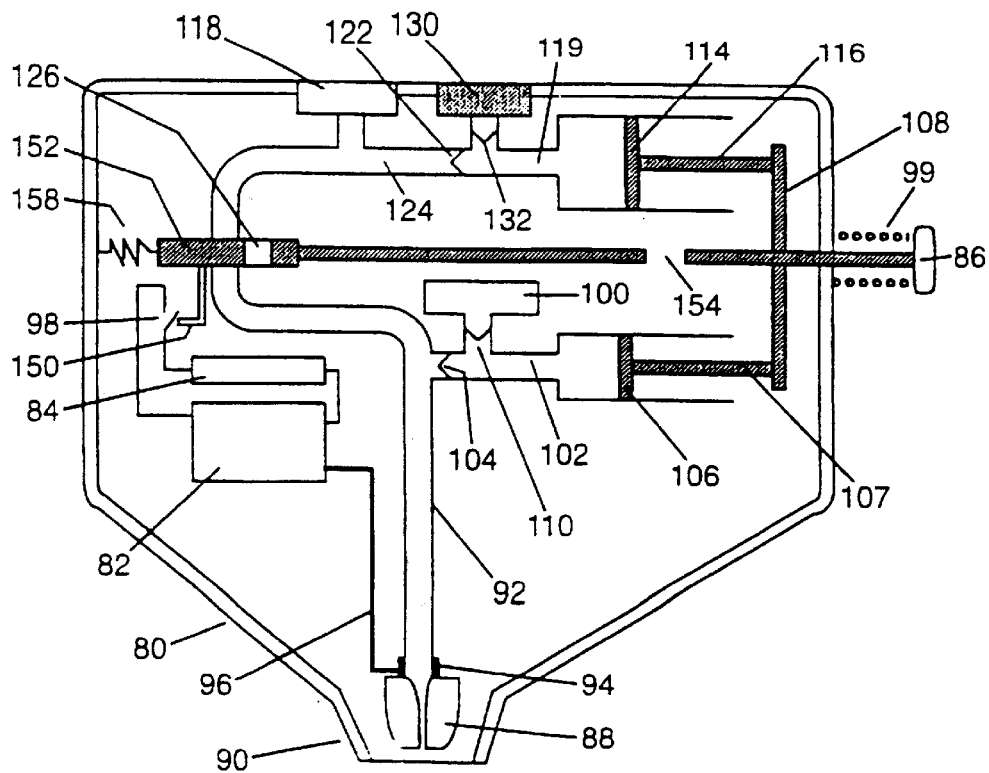

DISPENSING DEVICES

This invention relates to dispensing devices.

The invention has particular application to electrostatic spraying devices for use in applications involving for example air freshening, air purification, insecticide spraying, personal care/hygiene products (e.g. deodorants, cosmetics and perfumes) and medical and quasi-medical products such as nasal and respiratory tract sprays.

The present invention seeks to provide a device which is capable of efficiently delivering material in small amounts and/or in a relatively short duration of time.

EP-A-224352 discloses an electrostatic spraying device for dispensing opthalmically active compounds in discrete measured quantities. In the disclosed device, liquid is supplied to the tip of the nozzle and a potential difference is applied between the nozzle and an electrode spaced from the nozzle so that an electrical field of sufficient strength is provided at the outlet of the nozzle to draw the formulation away from the outlet as one or more ligaments which then break up into droplets. To enable the liquid to be drawn into ligaments, the liquid must be present at the very tip of the nozzle at the time of application of the potential difference. Liquid feed is supplied to the nozzle either from a reservoir of liquid within the device or by drawing the liquid from a separate source using a pipette action.

According to one aspect of the present invention there is provided an electrostatic spraying device comprising a nozzle, means for establishing a column of material to be sprayed within a passage leading to the nozzle outlet such that the leading surface of the column is spaced from the nozzle outlet, means for pneumatically ejecting said column or part thereof from the nozzle and means for applying high voltage to the material so that the spray formed by breaking up of the column on ejection from the nozzle are electrically charged.

According to a second aspect of the invention there is provided a method of electrostatic spraying comprising establishing a column of material to be sprayed within a passage leading to the outlet of a spraying nozzle of the device such that the leading surface of the column is spaced from the nozzle outlet, pneumatically ejecting the column of material or part thereof from the nozzle and applying high voltage to the material so that the spray particles formed by breaking up of the column on ejection from the nozzle are electrically charged.

Preferably the column of material is established in the passage as a discrete slug having a leading surface spaced from the nozzle outlet and a trailing surface to which air, gas or vapour under pressure can be applied to effect ejection of the slug from the nozzle.

According to a further aspect of the present invention there is provided an electrostatic spraying device comprising a nozzle, means for establishing a discrete slug of material to be sprayed within a passage leading to the nozzle outlet (preferably in such a way that the leading surface of the slug is spaced from the nozzle outlet), means for pneumatically ejecting said slug from the nozzle and means for applying high voltage to the material so that the spray particles formed by breaking up of the column on ejection from the nozzle are electrically charged.

Usually the material will comprise a single phase liquid formulation; however, we do not exclude application of the invention to materials in the form of liquid containing suspended solids. The formulation for instance may comprise more than one liquid in admixture—for example, the formulation may comprise an active ingredient such as a nasal decongestant agent, a diluent and other agents such as viscosity and/or resistivity modifying agents. Also we do not exclude the possibility of the material being in the form of pneumatically transportable fluent material other than a liquid, e.g. a powder.

In the device according to said one aspect of the present invention a column, preferably in the form of a discrete slug, of the material to be sprayed is established within the passage so that the column/slug is located with its leading surface (meniscus) spaced from the nozzle outlet. This allows the column/slug to be cleanly ejected from the nozzle outlet since the column/slug undergoes acceleration as it travels towards the nozzle tip and a relatively high velocity can therefore be imparted to the liquid before it reaches the nozzle tip. If for example a liquid is located with its leading meniscus at the nozzle tip prior to being displaced pneumatically, the liquid will have a low velocity at the beginning of the spraying operation and, in these circumstances, we have found that there is a tendency for spray attachment to the nozzle to occur at the beginning of the spraying action. Likewise, because the preferred method and device isolate a slug of the liquid within the passage leading to the nozzle outlet, the slug has a trailing surface and can exit cleanly from the nozzle without any significant tendency for spray attachment to occur, as would be the case for instance where the liquid in the passage is a continuation of, rather than being isolated from, the body of liquid from which it is derived.

Preferably the high voltage is applied to the material at or near to the nozzle outlet.

According to a narrower aspect of the invention there is provided an electrostatic spraying device comprising a nozzle, means for establishing a column of liquid within a passage leading to the outlet of the nozzle such that the leading surface of the slug is located upstream of a reduced cross-section portion leading to the nozzle outlet, means for pneumatically ejecting the slug as a jet from the nozzle and means for applying high voltage to the slug so that the droplets of the spray formed by breaking up of the jet are electrically charged.

Although not limited to any particular range of resistivity, the invention has particular application to low resistivity materials, especially liquids; e.g. liquids having a bulk resistivity of less than about $1\times10^7$ ohm cm including liquids having a resistivity significantly less than $1\times10^4$ ohm cm, e.g. $1\times10^3$ ohm cm and lower.

Preferably the arrangement is such that the jet of material at the point of egress from the nozzle has a diameter no greater than 300 micron and usually no less than about 15 micron. For example, the diameter of the jet at the point of egress may be in the range from about 20 to about 150 micron, more preferably 25 to 125 micron and most preferably 30 to 80 micron.

The nozzle design is preferably such that the surface of the nozzle at the point of egress of the material to be sprayed is not prone to create corona discharge. Thus as disclosed in prior EP-A-510725, bluff-ended nozzles are therefore preferred when the material to be sprayed has low resistivity.

The fluid pressure generated to effect pneumatic ejection of the slug is conveniently produced in response to operation of actuating means by the user and such operation of the actuating means may also be accompanied by priming of the passage leading to the nozzle outlet with the column/slug in preparation for pneumatic ejection. The priming action and fluid compression may occur substantially simultaneously and the arrangement may be such that operation of the actuating means is also accompanied by operation of a high voltage generator associated with the means for applying high voltage to the material to be sprayed whereby all of these operations together with ejection of the column/slug are effected in response to a single operation of the actuating means by the user. For example, the actuating means may normally be in a standby state and the arrangement may be such that operation of the actuating means is initially accompanied by compression of fluid and priming of the passage leading to the nozzle with the slug/column, followed by communication of the compressed fluid with the interior of the passage and by operation of the high voltage applying means so that, as the slug is displaced by the fluid pressure, the slug traverses a contact region at or in the immediate vicinity of the nozzle outlet where the high voltage is applied to the slug.

Instead of all operations being effected in response to a single operation on the part of the user, they may instead be decoupled. For example, at least priming of said passage with the slug/column may take place in response to operation of a first actuator, and the compression of the fluid (where necessary), application of high voltage and communication between the compressed fluid and the slug/column may take place in response to operation of a second actuator. Where the fluid used for ejection of the liquid is not pre-compressed but has to be compressed in the course of using the device, such compression may be effected in response to operation of the first actuator or the second actuator. Decoupled operation of the device in this way may be desirable where it is more convenient for the user to prime the device initially in preparation for use without necessarily having to locate the nozzle in any specific position before priming is effected, for instance as is required where the device functions as a nasal decongestant spray.

In one embodiment of the invention, the actuating means may be displaceable from a standby condition by the user and may be biassed to the standby condition, e.g. by spring loading, so that the actuating means automatically restores to the standby position following actuation by the user. Thus, for instance, user-effected displacement of the actuator from its standby condition may be accompanied by said fluid compression (and optionally by priming of said passage) and automatic return of the actuator may be accompanied by pneumatic ejection of, and application of high voltage to, the column or slug. Alternatively, user-effected displacement of the actuator in one direction from its standby condition may be accompanied by said fluid compression, ejection of the column or slug and application of the high voltage to the slug. The return stroke of the actuator may restore the device in preparation for the next dispensing operation and may for example be accompanied by disabling of the voltage supply and priming of the passage with a fresh slug/column.

Typically the pneumatic ejection will involve delivery of up to about 100 $\mu$l of the material from the nozzle. Usually the amount delivered on each operation will be a substantially constant volume in the range from about 2 to about 50 $\mu$l.

The material from which the nozzle is fabricated is desirably one to which the material to be sprayed is not prone to adhere, especially over that region of said passage which is occupied by the material prior to pneumatic ejection. In the case where the liquid to be sprayed is a liquid or liquid-based formulation, the nozzle is desirably fabricated at least in part from a hydrophobic material which has low wetting characteristics, such as PTFE. Alternatively the nozzle may be provided with a hydrophobic coating in said region and/or on its external surface around the nozzle outlet so as to suppress liquid "creep" and wetting. The coating may for instance be of an organo-silicon compound.

Preferably the tip region of the nozzle is of reduced diameter relative to that section of the nozzle upstream of the tip region. The diameter of the passage leading to the nozzle outlet will usually be sufficiently fine that any tendency for the pressurised fluid to by-pass the column or slug is avoided.

The device may be portable as a unit, i.e. the device may comprise a housing incorporating a high voltage generator, a reservoir for containing the material to be sprayed, the nozzle tube with means for transferring a column or slug of the material into the nozzle tube and means for pneumatically ejecting the column or slug of material from the nozzle outlet. In some applications, the device may be suitable for handheld use, preferably in such a way that operation of the device can be effected by manipulation of the device using the hand in which the device is held. Such manipulation may for example involve use of one of the fingers or the thumb to operate one or more actuators of the device.

In other applications of the invention, the device may be portable as a unit but may be designed for location on a support surface—for instance, the device may be used for dispensing formulations suitable for room fragrancing and/ or air purification in which case it may be designed for placement on a horizontal surface such as a window sill or shelf or for mounting on a vertical surface such as a wall.

In some instances, the device may not be portable as such but may be designed as a fixed unit for instance in the coating of articles or applying marking agents thereto. In this event, operation of the device may be initiated automatically by means of a sensor arranged to sense the presence of for instance the article at the location at which the coating or other formulation is to be applied to the article.

In each case mentioned above. i.e. portable, handheld and fixed devices, the operation of the device is conveniently initiated in response to actuation of a single or more than one actuator or sensor and the arrangement is such that actuation leads to initiation of the following steps:

transfer of the material to be sprayed into said passage;

pneumatic ejection of the column/slug; and application of the high voltage to the column/slug in the course of ejection.

The high voltage may be unipolar or it may be bipolar as disclosed in our prior EP-A-468735 and EP-A-468736, the entire disclosures of which are incorporated herein by this reference. Thus, the bipolar voltage may be employed to secure a measure of shock suppression and/or to facilitate the spraying of insulating targets (e.g. as in the case of a hair spray) as disclosed in EP-A-468735 and EP-A-468736. Where a bipolar source of voltage is employed, the arrangement is preferably such that successive slugs (or successive groups of slugs) of material discharged from the nozzle are charged with voltage of opposite polarity. Thus, means may be provided for coordinating the application of the voltage to the material being discharged with pneumatic ejection in such a way that successive slugs of the material (or successive groups of slugs) are charged with voltage of opposite polarity. This is particularly the case where each operation of the device results in the ejection of multiple slugs of material rather than just a single slug per operation of the device.

In the various aspects of the invention as defined above, preferably the arrangement is such that the voltage is applied to each slug of material only after the slug has been physically isolated from the reservoir of material within the device.

According to a further aspect of the present invention there is provided an electrostatic spraying device comprising a nozzle, a reservoir for containing material which is to be sprayed, a passage connecting the reservoir to the nozzle, means for establishing a column of said material to be sprayed within the passage such that the trailing surface of the column is separated from the remainder of the material in the reservoir whereby the gap affords electrical insulation between the tip of the nozzle and the reservoir, and means for applying high voltage to the column of material so that the spray particles formed by breaking up of the column on ejection from the nozzle are electrically charged.

In this manner, it is possible to secure electrical isolation of the material in the reservoir from the column or slug of material to which the high voltage is applied. This, in turn, permits the reservoir to be earthed if desired and the part of the device housing the reservoir may be held in the hand without necessarily having to insulate the user from the material in the reservoir. Such electrical isolation of the main body of material to be sprayed from the column or slug to which voltage is applied may be particularly advantageous since the capacitance of the device during spraying can be reduced significantly and more rapid build-up of the electric field is possible on application of the high voltage since the voltage is applied to a much smaller quantity of the material to be sprayed. Where the voltage is bipolar, the main body of the material stored in the device is not subject to the voltage swings that occur and because the slug of material can be ejected cleanly from the nozzle, there is a reduced tendency for spitting to occur.

Thus far, the invention has been defined in terms of producing a spray in which the spray particles are electrically charged by the application of high voltage. However, we do not exclude the possibility of eliminating the high voltage source. In this aspect of the invention there is provided a spraying device comprising a nozzle, a reservoir for containing material which is to be sprayed from the nozzle, means for priming a passage leading to the nozzle with material from the main body of material in the reservoir, and means for pneumatically ejecting the material so primed from the nozzle.

In this aspect of the invention, the material to be sprayed may for example comprise a liquid formulation in which case the liquid forms a spray as a result of hydraulic break-up. Where the material comprises a powder, the spray may form as a result of the powder becoming dispersed following ejection from the nozzle.

The invention will now be described by way of example with reference to the accompanying drawings, in which:

FIG. 1 is a schematic view of a nozzle for use in the present invention;

FIG. 2 is a view similar to that of FIG. 1 with the slug or column of liquid to be sprayed shown partly ejected from the nozzle;

FIG. 4 is a schematic view of another embodiment in which the sequence of operation is effected by means of a single actuator.

Figure 3:
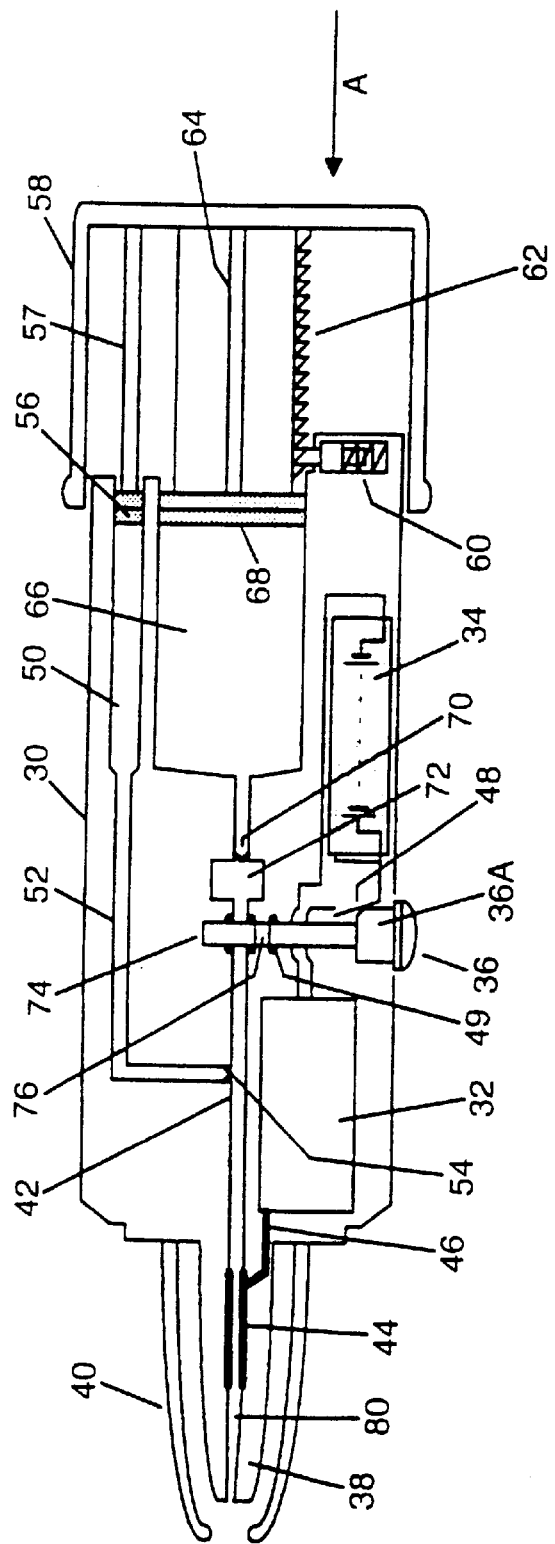
FIG. 3 is a schematic view showing an embodiment of the invention for use in the delivery of nasal decongestant or like formulations.
Figure 5:
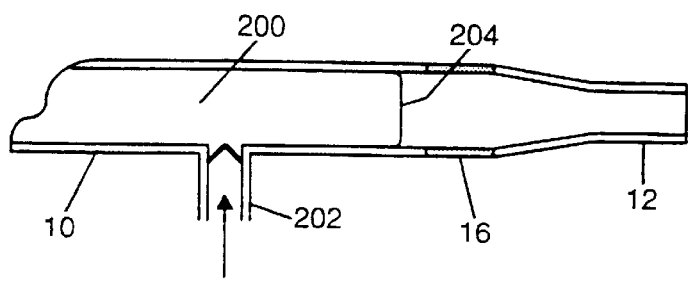
FIGS. 5 and 6 are views similar to those of FIGS. 1 and 2 but showing a modified method of liquid discharge.
Figure 6:
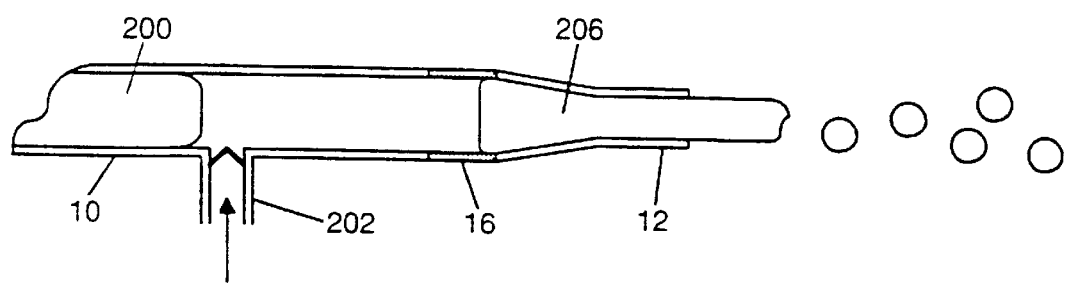

At FIG. 1 illustrates the principle of operation of devices in accordance with the present invention. The device comprises a nozzle tube 10 terminating in a tip 12 at one end which forms an outlet from which the liquid to be sprayed is dispensed in use. The liquid to be sprayed is established within the nozzle tube 10 as a column or slug 14 in such a way that the leading surface of the column 14 is spaced from the tip 12 of the nozzle. In this manner, a pocket of air is present between the leading surface of the column 14 and the nozzle tip. In addition, prior to or during the course of ejecting the column 14 from the nozzle tube 10, a pocket of air (or other gas or vapour) is established at the trailing surface of the column 14. The column 14 is expelled from the nozzle tube 10 by means of a pressurised gas or vapour applied to the trailing surface of the column 14 (see arrow P). The diameter of the tube 10 is sufficiently small that the pressurised gas or vapour cannot by-pass the column 14.

High voltage, e.g. typically of the order of 1 to 8 kV (but dependent on the particular application of the device) is applied to the nozzle tube by voltage generator (not shown). For this purpose the tube 10 includes a section 16 which is sufficiently electrically conductive for the designed purpose of applying high voltage to the liquid to be sprayed. The remainder of the tube upstream of the section 16 is fabricated from an electrically insulating material. The part of the tube downstream of the section 16 may be electrically insulating but preferably the downstream section will have some means of conducting voltage to the residual liquid in the downstream section after its trailing surface has cleared the electrode section 16. Thus, the tube section downstream of section 16 may be semi-conductive or may have a conductive or semiconductive track or the like along its inner surface.

In operation, when pressurised fluid is applied to the tube 10 the column 14 is displaced towards the nozzle tip 12 and passes through the section 16 where it is electrically charged. Prior to reaching the nozzle tip 12, the column 14 is accelerated by the pressurised fluid and consequently will be moving rapidly by the time the leading face of the column 14 reaches the nozzle tip. In this way, a clean start-up is achieved in the spraying operation since the liquid does not arrive at the nozzle tip until it has been accelerated. The column 14 on ejection from the tube 10 forms a stable jet 18 which breaks up into electrically charged particles which disperse as a spray. In the case of liquids, break up of the jet may be primarily hydraulic in nature or it may be influenced at least to some extent by the high potential gradient prevailing in the region of the nozzle tip relative to the surroundings or a target which is to be sprayed. In the latter case, the jet formed by the column as it emerges from the nozzle tip 12 may undergo some electrostatically induced necking in the manner disclosed in our prior EP-A-510725, the entire disclosure of which is incorporated herein by this reference.

Once the entire column 14 has been ejected, the pressurised fluid continues to discharge from the nozzle tip 12 and serves to purge the tube in readiness for the next operation. The purging action effected by the pressurised fluid reduces any tendency for stray liquid to remain in the vicinity of the nozzle tip 12 which could otherwise lead to untidy spray attachment to the nozzle tip at the end of the spraying operation and/or at the beginning of the following spraying operation. The nozzle tip 12 is desirably of reduced diameter as shown so that the column is "impact extruded" through the nozzle outlet thereby raising the velocity of the jet 18 further. Such reduction in the diameter of the nozzle tip 12 may be achieved by drawing down a tube at one end thereof or by moulding the tube with a blanked off end and then drilling a small diameter hole though the blanked off end by laser drilling or ultrasonic drilling.

Typically the volume of the column 14 will be substantially constant for a given application and will range from about 2 to 100 microliters, more usually from 2 to 50 microliters. With appropriate design of the nozzle, particularly the diameter of the outlet at the nozzle tip, materials with a wide range of volume resistivities can be sprayed successfully. In the case of liquids for instance, we have found that satisfactory spraying can be achieved with liquids having volume resistivities as low as $1\times10^3$ ohm cm and even lower (e.g. $2\times10^2$ ohm cm) although with resistivities as low as this, the "necking" effect referred to above is not usually observed. As disclosed in EP-A-510725, electrostatically induced necking is advantageous when very fine droplet sizes are required. Where very low resistivity liquids are employed, the absence of any significant electrostatically induced necking can be compensated for, if desired, by the use of a nozzle outlet of small diameter.

Typically the diameter of the outlet at the nozzle tip is no greater than 300 micron and usually no less than about 15 micron. For example, the outlet diameter may be in the range from about 20 to about 150 micron, more preferably 25 to 125 micron and most preferably 30 to 80 micron.

Referring to FIG. 3, the nasal sprayer comprises a housing 30 suitably dimensioned for hand held use. The housing accommodates a high voltage generator 32 and a low voltage battery supply 34 for powering the generator. The battery supply may comprise one or more replaceable batteries which may be of the rechargeable type if desired. The generator typically produces a high voltage output from about 1 to 3 kV up to about 12 to 15 kV, preferably from 2 or 3 kV to about 9 to 10 kV. Operation of the generator 32 is controlled by means of a switch actuator 36 suitably positioned for operation by the user while holding the device in one hand. In this embodiment, the switch actuator 36 is of the pushbutton type and is located generally centrally of the housing 10 for ease of operation with the the thumb or other fingers while holding the device in the palm of the hand. An earth return path may be established through the user for example by providing some form of contact on the housing 30, e.g. the switch actuator 36, so that when the device is held in the hand, a connection to earth is provided through the user.

The housing 30 is fabricated from a plastics material which has good electrical insulation properties and is designed in accordance with the teaching of our prior EP-A-441501 in order to allow the use of an inexpensive and compact generator. A nozzle 38 is provided at one end of the housing 30 and is located within a nose piece 40 which may be formed with one or more apertures (not shown) through which air can be drawn by the user in the course of inhaling through the nose. The nozzle 38 is conveniently fabricated from an electrically insulating, non-wetting plastics material (e.g. PTFE) and communicates with to an axially extending passageway 42 which may be in the form of a tube of electrically insulating material. In the vicinity of the tip of the nozzle 38, the passageway 42 is provided with an electrode 44 which may be cylindrical with an inside diameter corresponding generally to the inside diameter of the passageway 42. The electrode 44 is connected to the high voltage output of the generator 32 via lead 46. The generator 32 is energised by operation of the switch actuator 36, part 36A of which is arranged to effect closure of a switch contact 48 by a camming action as the actuator 36 is displaced inwardly relative to the housing against the action of a spring 49. Closure of contact 48 completes a circuit including the generator 32 and the low voltage source 34, thereby powering the generator. The generator may be of the design disclosed in EP-A-441501. The spring 49 serves to bias the switch actuator 36 to a position corresponding to deactivation of the generator 32.

Liquid from a reservoir 50 is supplied to the passageway 42 via tube 52 and one-way valve 54 in response to displacement of plunger 56 connected by stem 57 to a slidably mounted actuator 58 at the end of the housing remote from the nozzle end. The reservoir 50 may be a replaceable, "plug-in" cartridge. The actuator in this case is operable incrementally under the control of a detent 60 mounted in the housing for co-operation with a ratchet 62 provided internally of the actuator 58 which is in the form of a cap encircling the remote end of the housing. The liquid to be dispensed extends from the reservoir 50 through the tube 52 up to the valve 54 so that in response to each increment of movement of the actuator 58, a small slug of liquid is transferrred from tube 52 to prime the passageway 42 in the manner illustrated in FIG. 1.

Stepwise actuation of the actuator 58 also serves, through displacement of a plunger 68 mounted on stem 64, to pressurise air in a reservoir 66. The air passes via valve 70 into a pressure chamber 72 which can communicate with the passageway 42 under the control of a sliding valve 74 carried by the actuator 36. The valve 74 includes a port 76 which moves into registry with the passageway 42 when the actuator 36 is operated. Normally the valve 74 serves to isolate the pressure chamber 72 from the passageway 42. However, when the port 76 moves into registry with the passageway 42 and provides communication with the pressure chamber 72, a pulse of compressed air is injected which serves to eject the slug of liquid from the passageway. It will be noted that registry of the port 76 with the passageway 42 is accompanied by energisation of the generator and consequently high voltage is applied to the liquid through electrode 44 as the liquid travels toward the nozzle tip. At the point in time when the high voltage is applied to the liquid, the trailing surface of the slug will be downstream of the junction between the passage 42 and the passage 52 and hence the slug will be both physically and electrically isolated from the liquid in the passage 52 and the reservoir 50. Consequently, if the relevant components of the device are fabricated from an electrically insulating material, the liquid in reservoir 50 may be at or close to earth potential. The passage 80 in the nozzle tip is of reduced cross-section compared with the passageway 42 for the reasons mentioned in connection with embodiment illustrated in FIG. 1.

In operation, the user initially primes the device and compresses the air by operating the actuator 58, i.e. displacing it in the direction A in FIG. 3. This results in a slug of liquid being introduced into the passageway 42 in readiness for the next stage of operation. The user then registers the nosepiece 40 with the nostril which is to receive the spray and operates the actuator 36 which, during the initial part of its travel, operates switch 48 to activate the generator 32 and then moves port 76 into registry with passageway 42 allowing release of the air pulse from chamber 72 and consequent ejection of the liquid slug in the manner described with reference to FIG. 2. At the same time as operating the actuator 36, the user may inhale through the appropriate nozzle to produce an air flow through the nosepiece 40 to assist drawing the spray into the nasal cavity, although this is not essential to operation of the device. Because the spray droplets are electrically charged, they will rapidly deposit on the lining of the nasal cavity or within the upper respiratory tract thereby ensuring that penetration of the spray is limited.

Any tendency for deposition of the spray onto parts of the device during spraying can be reduced by fabricating the nose piece from a good electrically insulating material which will tend to hold any charge that it collects during spraying. Thus, when spraying commences corona effects lead to some charge deposition on the nose piece which, in turn, tends to repel the like-charged spray particles.

Referring to FIG. 4, this embodiment is similar to that of FIG. 3 but is configured to allow operation of the device by means of a single operation on the part of the user. The device comprises a housing 80 which is suitably dimensioned for hand held use and accommodates a high voltage generator 82 and a low voltage battery supply 84 for powering the generator. Operation of the generator 82 is controlled by means of a switch actuator 86 suitably positioned for operation by the user while holding the device in one hand. An earth return path may be established through the user for example by providing some form of contact on the housing 80 so that when the device is held in the hand, a connection to earth is provided through the user.

A nozzle 88 is provided at one end of the housing 80 and is located within a nose piece 90 which may be formed with one or more apertures (not shown) through which air can be drawn by the user in the course of inhaling through the nose. The nozzle 88 is conveniently fabricated from an electrically insulating, non-wetting plastics material (e.g. PTFE) and communicates with an axially extending passageway 92 which may be in the form of a tube of electrically insulating material In the vicinity of the tip of the nozzle 88, the passageway 92 is provided with an electrode 94 which may be cylindrical with an inside diameter corresponding generally to the inside diameter of the passageway 92. The terminal passageway 130 provided in the nozzle is of reduced cross-section for the reasons previously discussed. The electrode 94 is connected to the high voltage output of the generator 82 via lead 96. The generator 82 is energised by operation of the switch actuator 86 via an arm 150 mounted on a slide 152 after lost motion has been taken up, there being a gap 154 between the forward extremity of the actuator 86 and the slide 152. Thus, as the actuator 86 is displaced inwardly relative to the housing against the action of a spring 99, the forward extremity of the actuator 86 contacts slide 152 and displaces it to the left as viewed in FIG. 4 with consequent operation of the switch 98, activation of the generator 82 and hence application of high voltage to the electrode 94. Upon release of the actuator 86, the actuator and the slide 152 are restored to the positions shown by springs 99 and 158.

Liquid from a reservoir 100 (not necessarily to scale) is supplied to the passageway 92 via tube 102 and one-way valve 104 in response to displacement of plunger 106 connected to the actuator 86 by stem 107 and arm 108. The reservoir 100 may be in the form of a replaceable "plug-in" cartridge. The liquid in reservoir 100 is drawn via one-way valve 110 into tube 102 during the return motion of the actuator 86 and is injected as a slug into the passageway 92 in response to inward displacement of the actuator 86. The lost motion 154 introduces a delay between injection of the liquid into the passageway 92 and activation of the generator 82.

Inward displacement of the actuator 86 also serves, through displacement of a plunger 114 coupled to the actuator by stem 116 and arm 108, to maintain a supply of pressurised air in a reservoir 118 by feeding air via tube 119 and one-way valve 122 to reservoir 118 and associated tube 124. Tube 124 can communicate with tube 92 but is normally isolated from the latter by slide 152 which acts as a valve. Communication between tubes 124 and 92 is established when the slide is displaced sufficiently by the actuator 86 to bring a port 126 into registry with tube 124. This is phased in such a way that switch 150 is operated to activate generator 82 in advance of communication being established between tubes 124 and 92. Once communication is established, a pulse of air travels along passageway to eject the liquid slug in passageway 92 out of the nozzle 88 in the manner described in relation to FIGS. 1 and 2.

Air is drawn into the device through a filter 130 via valve 132 during return movement of the actuator 86 and hence plunger 114. The reservoir 118 may be provided with means for providing a visual indication that the reservoir is sufficiently pressurised to initiate dispensing operations. Initially before the device can be used for dispensing operations, the cylinder in which plunger 106 operates and the associated tube 102 must be filled (e.g. as part of the manufacturing process).

From the foregoing, it will be seen that the sequence of operations is effected in response to a single operation of the actuator 86. In this embodiment, once the device has been initially primed for use, the user would first register the nosepiece 90 with the appropriate nostril and then press the actuator 86 inwardly resulting in the following sequence:

- operation of plungers 106 and 114 with consequent injection of a liquid slug into tube 92 and pressurisation of the reservoir 118,
- activation of the generator to apply high voltage to electrode 94,
- transmission of an air pulse along tube 92,
- electrical charging of the liquid slug, and
- ejection and break up of the slug into a spray.

When the actuator 86 is released for return to the position shown, plungers 106 and 114 and slide valve 152 are all restored to the positions shown with accompanying replenishment of the liquid and air supplies in tubes 102 and 119 and deactivation of the generator 82.

In the embodiments described above, a discrete slug of liquid is injected into the passageway leading to the nozzle. In an alternative embodiment as illustrated in FIGS. 5 and 6, the arrangement is such that the liquid is established as a column within the passageway leading to the nozzle tip and not necessarily as a slug isolated from the liquid supply reservoir. Thus, as shown in FIG. 5 (where parts in common with the embodiment of FIG. 1 are depicted by the same reference numerals), prior to ejection a column 200 of liquid is established within the tube 10 which may (although this is not essential) extend without interruption from the main liquid reservoir. The column 200 is established in such a way that it extends beyond inlet 202 with its leading surface 204 retracted from the tip of the nozzle portion 12. The inlet 202 is connected to a source of pressurised fluid (e.g. air). When dispensing of the liquid as a spray is initiated, the air is injected through inlet 202 into the tube 10 so as to break into the column of liquid at that location and thereby isolate part 206 of the liquid which is then driven past the high voltage electrode 16 and out of the nozzle (see FIG. 6) to form an electrically charged spray of droplets.

What is claimed is:

1. An electrostatic spraying device for forming a spray from one discreet slug of material, the device comprising a nozzle; means for establishing the one discreet slug of said material to be sprayed within a passage leading to the nozzle outlet such that a leading surface of the one discreet slug is spaced from the nozzle outlet; means for ejecting the one discreet slug of material from the nozzle; and means for applying high voltage to the one discreet slug of material so that the spray particles formed by breaking up of the discreet slug on ejection from the nozzle are electrically charged.

2. A device as claimed in claim 1 in which the ejecting means comprises means for pneumatically ejecting said column/slug from the nozzle.

3. A device as claimed in any one of claim 2 in which the high voltage is applied to the column of material at or near to the nozzle outlet.

4. A device as claimed in any one of claims 3 in which the material is liquid; and a reduced cross-section portion is provided, leading to the nozzle outlet, the leading surface being located upstream of the reduced cross-section portion.

5. A device as claimed in any one of claim 4 in which the arrangement is such that the jet of material at the point of egress from the nozzle has a diameter no greater than 300 micron.

6. A device as claimed in any one of claims 5 in which ejection of the column/slug is produced in response to operation of actuating means by the user.

7. A device as claimed in claim 6 in which operation of the actuating means is accompanied by priming of the passage leading to the nozzle outlet with the column/slug in preparation for ejection.

8. A device as claimed in claim 7 in which operation of the actuating means is also accompanied by operation of a high voltage generator associated with the means for applying high voltage to the material to be sprayed whereby all of these operations together with ejection of the column/slug are effected in response to a single operation of the actuating means by The user.

9. A device as claimed in claim 7 in which ejection of the column or slug and/or application of the high voltage thereto are effected in response to a separate operation of the actuating means or operation of a different actuating means which effects priming and/or ejection.

10. A device as claimed in claim 1 in which the tip region of the nozzle is of reduced diameter relative to that section of the nozzle upstream of the tip region.

11. A device as claimed in claim 1 in which the high voltage is unipolar.

12. A device as claimed in any one of claims 11 in which the high voltage is bipolar.

13. A device as claimed in claim 12 in which the arrangement is such that successive columns/slugs (or successive groups of columns/slugs) of material discharged from the nozzle are charged with voltage of opposite polarity.

14. A device as claimed in claim 1 in which the material is discharged as a jet which, at the point of egress from the nozzle, has a diameter in the range from about 20 to about 150 micron.

15. A device as claimed in claim 14 in which the material is discharged as a jet which, at the point of egress from the nozzle, has a diameter in the range from 25 to 125 micron.

16. A device as claimed in claim 15 in which the material is discharged as a jet which, at the point of egress from the nozzle, has a diameter in the range from 30 to 80 micron.

17. A device as claimed in claim 1 in which the device additionally includes a reservoir for containing the material to be sprayed, the passage connecting the reservoir to the nozzle.

18. A device as claimed in claim 17 in which the trailing surface of the column/slug is isolated from the remainder of the material in the reservoir.

19. A device as claimed in claim 18 in which the trailing surface of the column/slug is physically isolated from the remainder of the material in the reservoir.

20. A device as claimed in claim 18 in which the trailing surface of the column/slug is electrically isolated from the remainder of the material in the reservoir.

21. A device as claimed in claim 18 in which the trailing surface of the column/slug is physically and electrically isolated from the remainder of the material in the reservoir.

22. A device as claimed in claim 1 in which the material to be sprayed is a liquid having a bulk resistivity of less than about $1 \times 10^7$ ohm cm.

23. A device as claimed in claim 21 in which the liquid has a bulk resistivity of less than $1 \times 10^4$ ohm cm.

24. A device as claimed in claim 23 in which the liquid has a bulk resistivity of $1 \times 10^3$ ohm cm or less.

* * * * *